(12) United States Patent
Espejord

(10) Patent No.: US 8,816,705 B2
(45) Date of Patent: Aug. 26, 2014

(54) METHOD AND DEVICE FOR MONITORING A ZONE OF METAL

(75) Inventor: Olav Espejord, Trondheim (NO)

(73) Assignee: Roxar Flow Measurement AS., Stavanger (NO)

( * ) Notice: Subject to any disclaimer, the term of this patent is extended or adjusted under 35 U.S.C. 154(b) by 184 days.

(21) Appl. No.: 12/567,248

(22) Filed: Sep. 25, 2009

(65) Prior Publication Data
US 2011/0001498 A1    Jan. 6, 2011

(30) Foreign Application Priority Data
Jul. 3, 2009 (NO) .................................... 20092518

(51) Int. Cl.
*G01R 27/14* (2006.01)
*G01N 27/20* (2006.01)

(52) U.S. Cl.
CPC ...................................... *G01N 27/20* (2013.01)
USPC ............................. 324/693; 324/700; 702/57

(58) Field of Classification Search
USPC .................................................. 324/693, 700
See application file for complete search history.

(56) References Cited

U.S. PATENT DOCUMENTS

| 2,094,234 A | 9/1937 | Drain, Jr. |
| 4,656,595 A | 4/1987 | Hognestad |
| 4,914,378 A | 4/1990 | Hayashi et al. |
| 6,861,853 B2 * | 3/2005 | Hands .......................... 324/700 |
| 6,922,641 B2 | 7/2005 | Batzinger et al. |
| 2005/0075800 A1 * | 4/2005 | Batzinger et al. ............... 702/35 |

FOREIGN PATENT DOCUMENTS

| JP | 2005-208039 | 8/2005 |
| JP | 2008-191169 | 8/2008 |
| JP | 2009-74923 | 4/2009 |
| WO | WO 03/019167 | 3/2003 |
| WO | WO 2007/088913 | 8/2007 |

* cited by examiner

*Primary Examiner* — Arleen M Vazquez
*Assistant Examiner* — Feba Pothen
(74) *Attorney, Agent, or Firm* — Ladas & Parry LLP

(57) ABSTRACT

Method and device for monitoring a zone of a metal structure in terms of its electrical resistance in order to detect possible defects in the structure, by periodically passing current through the zone in different directions while measuring and recording voltage drops in a number of selected unit areas ($a_{ij}$) within the zone, and by combining, for each unit area ($a_{ij}$), at least two measured values recorded during at least two measurements made with current passing in different directions, and by comparing values obtained by at least one similarly obtained value made earlier.

10 Claims, 3 Drawing Sheets

METHOD AND DEVICE FOR MONITORING A ZONE OF METAL

BACKGROUND OF THE INVENTION

Large metal structures in offshore environments or other tough or hazardous environments are subject to heavy wear and corrosion and need to be monitored during their lifetime in order to maintain safety for personnel and security for operation. Examples in this respect are large vessels and offshore petroleum production structures.

Various measuring principles of such monitoring systems have been suggested, i.e. methods based on vibration analysis, acoustic emission, ultrasonic systems, registration of magnetic fields as well as visual inspection. In general, these methods have not been adequate, mainly because of the great strains to which the monitoring equipment can be exposed, in particular under water. In addition to being resistant to such strains, it is also important that the monitoring systems do not entail prohibitive installation and maintenance costs, since the components or areas which are to be monitored often have very large dimensions. Systems that, for example, are based on the use of a number of transducers, e.g. for detection of vibration, acoustic emission or ultrasonic signals, may involve the mounting of a large number of transducers, each one representing a comparatively high expense and a risk of failure.

Another previously disclosed method for examination of cracks in structural parts or components is based on the measurement of the electric field that is produced in the structure. This so-called potential drop method is used for detailed examination of a crack that has been localized beforehand. The size or depth of the crack is determined by means of contact points on each side of the crack, between which the voltage is measured. The supplied current is either DC or AC with a low frequency. Different versions of the potential drop method have been published in German Patent Application No. 25 57 658 and in United Kingdom Patent Specification No. 804323. In the former publication, a high frequency current supply is used, and the examination comprises measurements of the drop of potential as a function of the frequency. In the latter case, which in particular has been reported to concern surface cracks, a radio frequency potential is measured, which potential occurs between two separate electrodes that are moved on the surface of the structure while an oscillating electric current is supplied thereto from a source of radio frequency. Such an arrangement with movable electrodes which are to be guided all over the monitoring area cannot, however, be used for the purpose mentioned above.

In the 1980's a refined version of the potential drop method was developed, by the inventor denoted "the fingerprint method", as described in U.S. Pat. No. 4,656,595 (Hognestad).

According to this method electric current is supplied to a steel structure which is equipped with contact points between which are measured voltage drops caused by the impressed current. A relatively large number of fixed contact points are used all over the area which is to be monitored. The voltage drops are measured between selected pairs of contact points and these voltage drops are compared with corresponding voltage drops that have been measured previously in the same manner when the structure was in an initial condition, preferably without any defects. The monitoring can thus be performed by means of robust and simple devices which are relatively impervious to rough environments. Though this method provided a substantial improvement over the earlier techniques, it still did not provide an efficient means for early detection of spot damages to the structure or defects that occurred as mainly linear cracks in the direction of the current passing therethrough.

SUMMARY OF THE INVENTION

An object of the present invention is to provide a method and an apparatus for examination of metal structure with respect to defects, which is more reliable than existing methods, systems and apparatuses.

A specific object is to provide a method and an apparatus as mentioned above which is able to reliably detect also relatively small, longitudinal cracks and spot corrosion.

The above mentioned objects are achieved by the method according to the invention of monitoring a zone of a metal structure in terms of its electrical resistance in order to detect possible defects in the structure, by periodically passing current through the zone in different directions while measuring and recording voltage drops in a number of selected unit areas within the zone, and by combining, for each unit area, at least two measured values recorded during at least two measurements made with current passing in different directions, and by comparing values obtained by at least one similarly obtained value made earlier.

The invention is also directed to a device for a carrying out the method comprising a means for supplying electric current, electrical conductors connected between said supply means of electric current and electric supply contacts on the metal structure, as well as a number of contact points arranged on the metal surface. The contact points are arranged in rows and columns forming a matrix pattern in which the contact points in each adjacent two rows are mutually displaced in relation to one another so that each column of contact points is comprises by contact points in every second row of the matrix, thus forming unit areas surrounded by four neighboring contact points belonging to three different matrix rows. The device further comprises a first set of current supply contacts at opposite sides of the matrix in a direction parallel with the matrix rows and a second set of current supply contacts at opposite sides of the matrix in a direction parallel with the matrix columns, as well as means to switch the current supply between the first and the second set of current supply contacts to allow repeated measurements of voltage drop across each unit area ($a_{ij}$) in transverse directions.

By the term "defects" in a structure as used herein is meant any kind of flaw or damage irrespective of their nature or origin, including, but not limited to damages caused by corrosion, damages in the form of cracks or pinholes, damages caused by general wear over time and damages caused by impacts of any kind.

By the term "combining" two measured values as used herein is understood any technical means to derive more information from the two measurements held together than what is possible to derive from either one of them alone. A typical way of combining two measured values is to simply compare them. Are they of the same approximate magnitude (in relation to their respective initial fingerprint value). If there is a deviation in the two relative values, taken into account their initial values, by more than a certain set percent, then at least there is a need for further investigation. An obvious way of combining two measured values would be to add the two values and to relate to their sum value. Why this is particularly meaningful in the case of the present invention, is explained in more detail in relation to FIGS. 3a-3c.

By the term "comparing values obtained," it is understood that the comparison at least may relate to either or both of a)

a comparison between change compared to any initial value in voltage drop in horizontal direction relatively to change in voltage drop in vertical direction and b) a change compared to any initial value in the sum of corresponding two voltage drops.

While any combination, comparison and adding of values may be performed manually or automatically, the typical situation in an industrial examination is naturally that a computer performs both the calculation and at least a preliminary assessment of status for any unit area. Such a computer may also be programmed to automatically produce reports of failure and draw 2D or 3D graphs that illustrate any given values and particularly any values indicating a defect in the structure being examined.

While in this description we generally refer to the measured values as potential drops, any values derived from such potential drop may be used instead. In practice, typically a dimensionless function denoted "Fc" is used, which is defined in manner that a number 0 for this function indicates "no change" while a factor 1000 indicates that half of the effective wall thickness is lost or corroded. Any other function derived from the potential drop(s) may be used instead.

The term "horizontal" as used in relation to the matrix contact points (contact points for short) herein is understood to mean the direction along the rows of the contact points, as indicated by the arrow R in FIG. 1, irrespective of the physical orientation of the pipeline section. Similarly, by "vertical" in relation to the contact points is understood the direction along the columns of the contact points. The terms "horizontal" and "vertical" thus only refer to the orientation on the drawings, not the physical orientation.

DESCRIPTION OF THE PREFERRED EMBODIMENTS

Figures 1, 2:
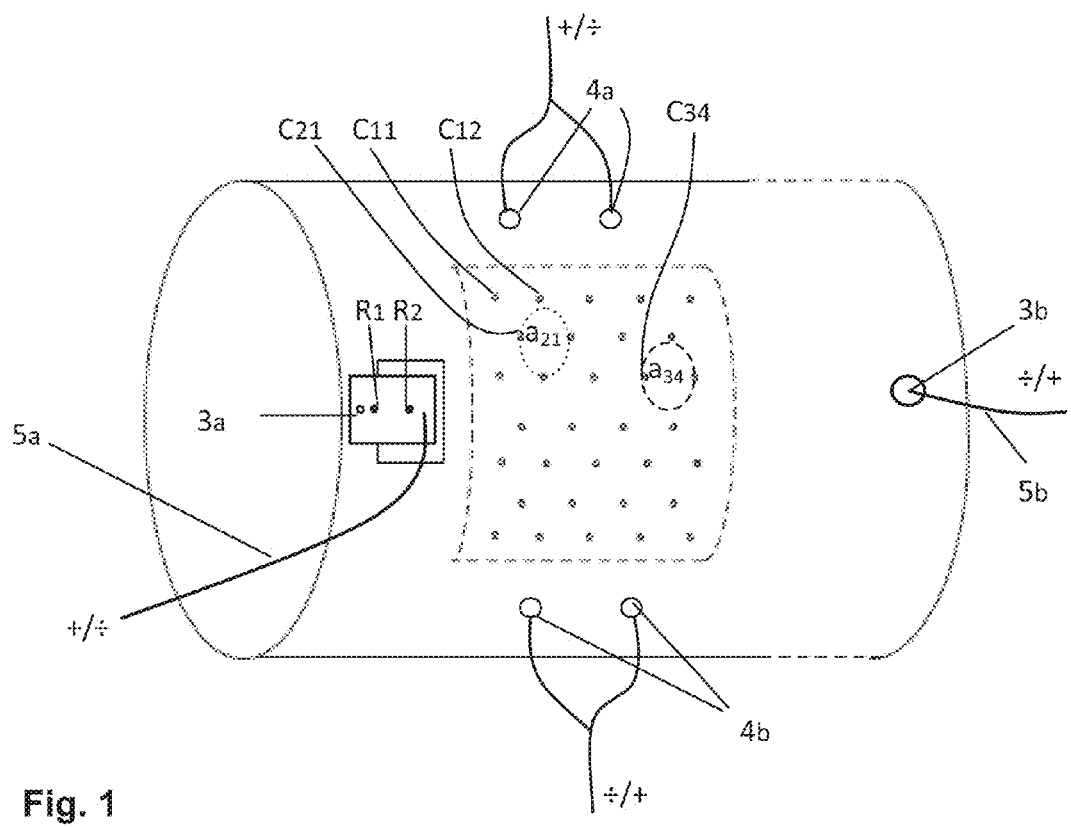
FIG. 1 is a perspective illustration of a pipeline section provided with measurement equipment according to the present invention.
FIG. 2 is a diagrammatic representation of the matrix area of the measurement equipment according to the present invention.

FIG. 1 shows a metal pipeline section 1 to be monitored with respect to possible defects or damages according to the present invention. A measurement area 2 is provided with a matrix of contact points $C_{ij}$ arranged in a pattern and connected to measurement equipment (not shown) able to measure electric potential (voltage drop) between pairs of contact points. The first contact point in the first row is labelled $C_{11}$ in which the first index numbers the row and second index numbers the column, which is a common way of indexing points in a two dimensional matrix. Hence the fourth contact point from the left in the third row is labelled $C_{34}$. An arbitrary contact point is indicated by the indices "i" and "j", $C_{ij}$.

The first contact point in the rows 2, 4, 6, i.e. $C_{21}, C_{41}, C_{61}$ respectively, are not vertically in line with the first contact points of rows 1, 3 and 5 etc., i.e. $C_{11}, C_{31}, C_{51}$, but displaced to the right by a distance corresponding to half the horizontal distance between two adjacent contact points. The distance between adjacent contact points in each and any row, is typically uniform. Correspondingly all contact points in rows of even numbers are similarly displaced in relation to the contact points in rows of odd numbers. This has the function of "isolating" unit areas $a_{ij}$ between two adjacent contact points in a row. As an example, unit area $a_{21}$ is surrounded by contact points $C_{21}$ and $C_{22}$ horizontally and by contact points $C_{12}$ and $C_{32}$ vertically. The concept of defining unit areas in this manner is essential with the present invention, in the sense that each unit area is monitored by measuring voltage drops when passing a current through the area in transverse directions and to assess possible damage to the area by the combined measurement.

Although referred to as a "matrix", the matrix of contact points as here described may actually, due to the horizontal displacement in every second row, be seen as a combination of two matrices merged together. One consequence of the displacement of contact points in every second row is that— when regarding the individual columns of the matrix—the first column of the combined matrix only comprises contact points in uneven numbered rows, the second column only comprises contact points in even numbered rows, etc. Therefore—and this would be quite confusing if the matrix were to be treated as such in a strict mathematical sense—the second column in the matrix comprises contact points $C_{21}, C_{41}, C_{61}$, while one would expect the second digit of the index to be 2, not 1. The third column of the matrix comprises contact points $C_{12}, C_{32}, C_{52}$, etc while one expect the second digit of the index to be 3, and so on. However, since the matrix of the invention is not used for matrix calculations, just for calculations between adjacent pairs of contact points, this irregularity does not matter. It is not important for the present invention whether the pattern of contact points really constitute a matrix in a mathematical sense of the word; it is simply a way of indicating the distribution of contact points in two dimensions.

It is only possible to define unit areas in this way where there are four contact points surrounding such an area; therefore there are no unit areas above contact point $C_{21}, C_{22}$, etc., as these areas are only surrounded by three contact points each. Similar considerations apply at the right hand side of the matrix, at the left hand side and at the bottom of the matrix.

In order not to overload FIG. 1 with symbols, only a couple a couple of unit areas, $a_{21}$ and $a_{34}$, are illustrated, but it should be understood that there are similar unit areas between all contact points except for—as explained above—in the first and last row and in the first and the last column of the matrix.

At both sides of the matrix of contact points, horizontally, a first set of electric current supply contacts (current contacts for short) 3a, 3b are attached to the metal structure, comprising at least one current contact on each side of the matrix, to which conductors 5a, 5b from a current source are connected, so that a potential may be set up in the metal structure across the matrix in a direction substantially parallel with the rows of contact points of the matrix. This first set of current contacts may thus be said to be arranged in the direction of the rows of the matrix of contact points.

Furthermore, at both sides of the matrix in the direction of the columns of the matrix of contact points, a second set of current contacts 4a, 4b are arranged, comprising at least one contact on each side of the matrix, to which conductors from a current source are connected. In this way, a potential may be set up in the metal structure across the matrix in a direction mainly perpendicular to the potential set up by the first set of current contacts. The current source for the second set of current contacts may be the same as that used to set up a potential in the direction of the row of the matrix, or it may be a different one. In use of the device according to the present invention, there is no need to supply potential in the two directions at the same time, therefore one current source together with required circuitry and switches will adequately be able to serve all current contacts.

In FIG. 1, the second set of current contacts 4a, 4b comprises two contacts each in order to obtain relatively equal potential along imaginary lines parallel with the matrix rows. Each second set of current contacts may also comprise three or more individual current contacts along a line parallel to the matrix rows.

Resistance in metal structures depends largely upon temperature, and in order to have a system that is reliable under practically variable conditions, the systems should preferably be arranged to compensate for such effects. One way of obtaining such compensation is to include a set of reference electrodes (contact points) $R_1$, $R_2$ as shown at current contact 3a in FIG. 1. Instead of measuring just the individual voltage drops between each pair of contact points in the matrix rows, the ratio $\Delta U_{h\ ij}/\Delta U_{ref}$ may be measured and recorded, in which $\Delta U_{ref}$ is the voltage drop between the contact points $R_1$ and $R_2$, electrically isolated from the metal structure, but arranged by it as to have the same temperature as the part of the structure where the matrix is attached, while $\Delta U_{h\ ij}$ is the voltage drop measured between any two adjacent contact points in a matrix row during the same measuring cycle that $\Delta U_{ref}$ is measured.

Another way of compensating the general temperature variation in the structure is by also measuring the entire voltage drop between the respective current contacts, e.g. between the current contacts 4a and 4b when measuring in the matrix column direction, and instead of recording simply the voltage drops between pairs of adjacent contact points in each column, by recording the ratio $\Delta U_{v\ ij}/\Delta U_{total}$ where $\Delta U_{v\ ij}$ is the measured voltage drop between any two adjacent contact points in any column of the matrix while $\Delta U_{total}$ is the voltage drop between 4a and 4b during the same measuring cycle.

We now refer to FIG. 2 which is a diagrammatic illustration of a matrix of contact points and corresponding unit areas as shown in FIG. 1, folded out to a flat surface. It is incidentally evident for a person skilled in the art that the method according to the present invention is applicable to flat surfaces as well as to curved surfaces, such as the pipeline section illustrated by FIG. 1.

In the enclosed drawings each individual unit area is given same index as the contact point to its immediate left. As earlier explained there are no unit areas in the first row, hence no unit area denoted $a_{11}$, $a_{12}$, or $a_{13}$ etc. Correspondingly there are no unit areas in the first column, i.e. the first column of contact points in uneven numbered rows. The second column of the matrix is made up by the leftmost contact points in the even numbered rows, $C_{21}$, $C_{41}$, $C_{61}$, etc. In this column we find unit areas $a_{31}$, $a_{51}$, etc above and below said contact points.

Again, not to overload the drawings with information, only some of these unit areas are illustrated, but it is understood that any space or area surrounded by two contact points horizontally and by two contact points vertically, is a unit area according to the present invention.

Figure 3A:
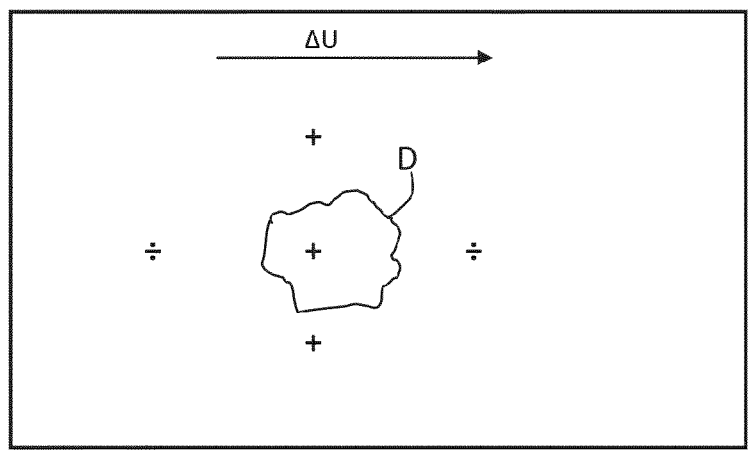
FIGS. 3A-3C are diagrammatic representations elaborating a benefit of the present invention over a prior art measurement technique.

FIG. 3a illustrates the change of voltage drop in and around a defect zone when measuring with current travelling in one direction (horizontally in the drawing). The symbol $\Delta U$ indicates a voltage drop from left to right in the drawing. The defect area D exhibits a higher resistance and therefore the voltage drop in this area will show an increase (+). Ideally this should have been the only change observed and the interpretation of the measurements would have been easy. However, the increased resistance in an area leads to an increase in the total resistance along the line of the current travelling through that area, which means that slightly less current will travel through this area and slightly more current will travel through undamaged neighboring areas above and below. When slightly less current travels through undamaged areas, the voltage drops in such areas are somewhat reduced, as illustrated by the negative signs to the left and to the right of the damaged zone in FIG. 3a. Furthermore, when slightly more current travels around the damaged area, above and below the area as illustrated in FIG. 3a, then the voltage drops in these areas show a slight increase. This means that not only the area of the defect but all areas close to the defective area, are more or less influenced by the damage, with regard to their voltage drops. The readings are therefore not always easy to detect and also difficult to exactly locate.

Figure 3B:
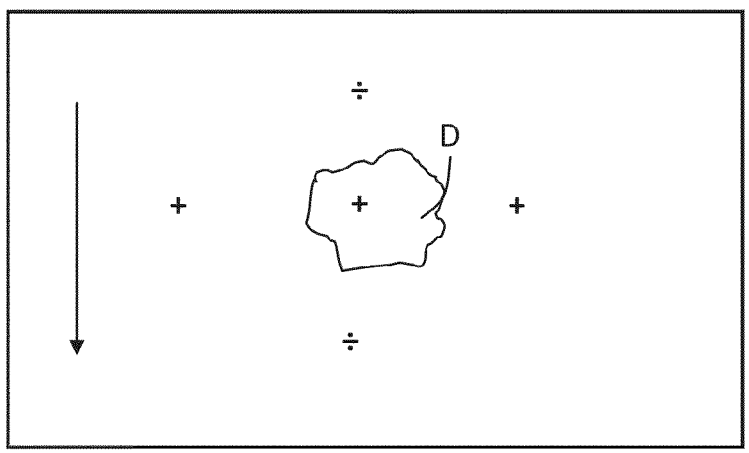

FIG. 3b is similar to FIG. 3a with the exception that the current is set to travel vertically in the drawing thus leading to an increase in the voltage drops to the right and to the left of the damage and a reduction in voltage drop in the area in front of and behind the damaged zone seen in the direction of the travelling current, i.e. vertically (in the drawing) above and below the defective area D.

Figure 3C:
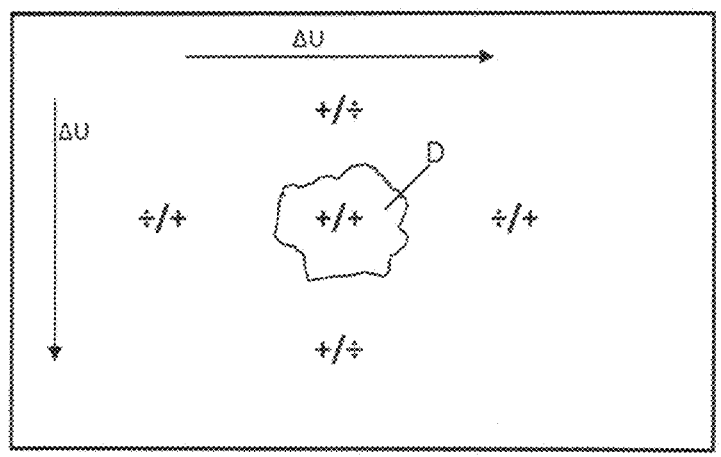

FIG. 3c may be seen as a combination of FIG. 3a and FIG. 3b and gives an indication of the benefit achieved by measuring in transverse direction and using the combined results to assess if and where a defect is localized. The undamaged areas surrounding the defective area will exhibit "opposite" behavior when measured vertically from the behavior when measured horizontally. Simple addition of the two measurements will therefore lead to measured value showing little or no change, and the area will be recognized as healthy. The only area exhibiting increase in voltage drop when measured in both directions is the defective or damaged one, therefore addition of the results of measurements in transverse directions will enhance the indication of this area as being a damaged area.

EXAMPLE

A metal pipeline structure is provided with a matrix of contact points as illustrated in FIG. 1. It need not be a mainly vertical side of the pipeline, it may well be covering an area across the lowermost line of the pipeline cross-section, where traces of water and sand will typically accumulate and where corrosion to the structure therefore will most likely occur.

When the pipeline is installed, the matrix of contact points are attached and when the pipeline is set in production, the measurements commence and the "fingerprints" of all the unit areas in the matrix of contact points are recorded when measuring with current travelling in the direction of length of the pipeline. Instead of recording just the individual voltage drops in each unit area, what is recorded is the ratio between the individual voltage drops and the voltage drop between the reference electrodes $R_1$ and $R_2$: $\Delta U_{h\ ij}/\Delta U_{h\ ref}$, the index h indicating that the measurement is made with current travelling in the direction of the matrix rows (or horizontally). Similarly $\Delta Uv_{ij}$ would mean a voltage drop across a unit area in a direction between to contact points in a matrix column, and just $\Delta U_{ij}$ would mean a potential drop over a unit area in either direction, row or column of the matrix.

In order to make an additional improvement to the exactness of the measurement, measurements are made twice, first with current travelling from current supply contact 3a to current supply contact 3b, and thereafter, with the same magnitude of current travelling in the opposite direction. The mean of the absolute values of the above defined ratio for the two measurements is used as one "fingerprint". The point of performing measurements with current travelling in opposite directions is to eliminate so-called thermoelectrical effects, further improving the reliability of the measured values.

Correspondingly, another fingerprint is obtained by supplying current through the structure in the direction of the matrix rows, and preferably again by using an average from measurements made with current travelling in opposite directions. And again, it is not the simple voltage drops that are recorded, but a ratio that compensates for temperature variations. The compensation could be made by use of another pair of reference electrodes, but it could also be made by measuring the entire voltage drop between the current supply electrodes 4a and 4b, and recording the ratio $\Delta U_{v\,i}/\Delta U_{v\,total}$ as a second fingerprint, the index v indicating that the measurement is made with current travelling in the direction of the matrix columns.

Periodically through the lifetime of the structure similar measurements are repeated and the results thereof recorded and compared with the initial measurement, the fingerprints. The periods may be set to be just seconds or minutes or up to several days, depending upon the nature of the structure, its position, its use, the potential damage to be expected, etc. A person skilled in the art will understand that the comparison of results are preferably carried out by a computer that is programmed to rapidly and reliable compare results and to make alerts when deviations of a certain magnitude are observed.

Addition of the values measured horizontally and the values measured vertically to improve the reliability is made either consistently or whenever a deviation is observed either in a horizontal or a vertical measurement or both. The results may also be shown graphically, typically as bars whose heights represent the mentioned ratios based on voltage drops, and using colour or other means to pedagogically allow immediate comparison of fingerprint(s) with fresh measurements.

Figure 4:
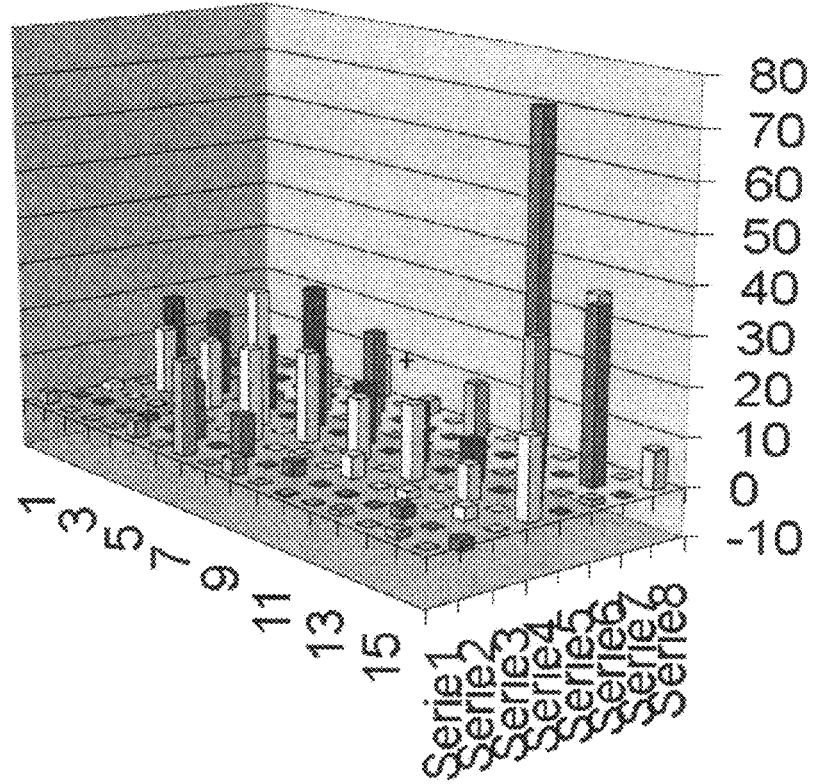
FIG. 4 is a chart showing data based comparison of measurements with fingerprint measurements.

FIG. 4 shows a 3D bar graph based on a series of measurements made horizontally and vertically and is an illustration on how effective and pedagogical any defects are visualized by bars becoming too tall.

A person skilled in the art will readily understand the order of measurement is of no significance, hence the measurement of voltage drops may well be performed first in the direction of the matrix columns first and along the matrix rows thereafter without compromising the scope of the invention, nor its effectiveness.

While temperature compensation is exemplified in one manner (reference electrodes) for the direction of the matrix rows and in another manner (total voltage drop) for the direction of the matrix columns, a person skilled in the art would readily understand that either type of compensation may be used for either direction.

Example of Calculation Method

Any voltage measurement, from the matrix contact points as well as from reference electrodes or between current supply contacts, is made as follows:

$$U=ABS(u1-u2)$$

Where u1 is the voltage drop between two contact points when current is passed in one direction and u2 is the voltage drop between same contact points when current is passed in the opposite direction.

In addition we establish the following parameters:
Rs is the voltage drop between the reference electrodes in its initial condition, Rn is the voltage drop between the reference electrodes for any given later measurement, Ms is the voltage drop in one direction across a unit area in its initial condition, Mn is the voltage drop in one direction across that unit area during any given later measurement, $Fc_h$ is Fc value for a horizontal (longitudinal) measurement, $Fc_v$ is Fc value for a vertical (transversal) measurement, $Fc_c$ is the Fc value as combined by the two fore mentioned Fc values, Firstly the two individual Fc values are calculated separately.

$$Fc_h=(((Rs_h/Ms_h)*(Mn_h/Rn_h))-1)*1000$$

Where $Rs_h$, $Ms_h$, $Mn_h$ and $Rn_h$ all are horizontal (longitudinal) measurements, and $$Fc_v=(((Rs_v/Ms_v)*(Mn_v/Rn_v))-1)*1000$$

Where $Rs_v$, $Ms_v$, $Mn_v$ and $Rn_v$ all are vertical (transversal) measurements, Thereafter the individual Fc values are combined e.g. by addition:

$$Fc_c=Fc_h+Fc_v$$

The $Fc_c$ value does not need to be compared with an initial value since it is combined from two parameters that already have been. This means that any change from zero of the $Fc_c$ value is an indication of actual change in the structure being examined. Thus, any measured Fc value larger than a predefined maximum can be used as an "alarm" level at which further investigations are initiated.

It will be understood by persons skilled in the art that the use of Fc values only represent one practical way of simplifying the task of mathematically comparing voltage drops and that, therefore, the discussion of the invention in general terms rather relate to voltage drops than to the derived Fc values.

What is claimed is:

1. A method of monitoring a zone of a metal structure in terms of its electrical resistance in order to detect possible defects in the structure, by periodically passing current through the zone in different directions while measuring and recording voltage drops in a number of selected unit areas surrounded by four neighboring points arranged in a matrix-like pattern and belonging to three different matrix rows within the zone, and by combining, for each unit area, at least two measured values recorded during at least two measurements made with current passing in different directions, and by comparing values obtained by at least one similarly obtained value made earlier;

for each unit area, combining the recorded values to obtain a sum value for each unit area; and to assess possible defects in each unit area, comparing the sum value obtained during a recent measurement with a sum value obtained for same unit area during an earlier, similar measurement.

2. The method as claimed in claim 1, wherein a number derived from the measured value is a number expressing a ratio between a measured value of voltage drop and a value measured to compensate for temperature variations.

3. The method as claimed in claim 2, wherein the value measured to compensate for temperature variations is obtained by passing the current to the current supply contacts via another metal structure electrically isolated from the monitored metal structure and comprising reference electrodes, and during each measurement of voltage drops over unit areas also measure and record the voltage drop between the reference electrodes.

4. The method as claimed in claim 2, wherein the value measured to compensate for temperature variations is obtained by during each measurement of voltage drop over unit areas also measure and record the total voltage drop between the electric current supply contacts.

5. The method as claimed in claim 1, wherein contact points are arranged in rows and columns in the zone to form a matrix like pattern in which the contact points in each adjacent two rows are mutually displaced in relation to one another, thus forming unit areas between groups of four neighboring contact points, namely two adjacent contact points in a common row, one contact point in the row above said common row and one contact point in the row below said common row, and in one period supplying an electric current to a first set of current supply contacts at opposite sides of the zone, to set up a voltage drop in a direction parallel with the rows of the matrix of contact points and to measure the voltage drops in each unit area during that period and to record these values or values derived from these values, in another period supplying an electric current to a second set of current supply contacts at opposite sides of the metal structure, to set up a voltage drop in a direction parallel with the columns of the matrix of contact points and to measure the voltage drops in each unit area during that period and to record these values or values derived from these values.

6. The method as claimed in claim 1, wherein a pulsed square wave current is supplied with a rate allowing steady state conditions to be reached with respect to voltage drops before each measurement is made.

7. The method as claimed in claim 1, wherein, for each voltage drop determination, current is first passed in one direction through the metal structure and a first measurement is made, whereafter current is passed in the opposite direction through the metal structure and a second measurement is made, whereafter the adequate voltage drop for each unit area is taken as the calculated average of the two voltage drop measurements.

8. The method as claimed claim 1, wherein an initial state or reference state of the construction is made by a first set of measurements determining initial voltage drops, whereafter all subsequent measurements are compared with the reference state in order to assess occurrence of defects in the structure.

9. The method as claimed in claim 1, wherein a computer is used for one or more of the tasks of controlling the current supply, of recording the measured potential drops, of combining the recorded values of potential drops and of assessing whether any unit area is defective.

10. A device for monitoring electrical resistance in a zone of a metal structure, comprising a means for supplying electric current, electrical conductors connected between said supply means of electric current and electric supply contacts on the metal structure, as well as a number of contact points arranged on the metal surface, wherein said contact points are arranged in rows and columns forming a matrix pattern in which the contact points in each adjacent two rows are mutually displaced in relation to one another so that each column of contact points is comprises by contact points in every second row of the matrix, thus forming unit areas surrounded by four neighboring contact points belonging to three different matrix rows, further comprising a first set of current supply contacts at opposite sides of the matrix in a direction parallel with the matrix rows and a second set of current supply contacts at opposite sides of the matrix in a direction parallel with the matrix columns, as well as means to change the switch the current supply between the first and the second set of current supply contacts to allow repeated measurements of voltage drop across each unit area in transverse directions; and to assess possible defects in each unit area, comparing a sum value obtained by combining repeated measurements during a recent measurement with a sum value obtained by combining repeated measurements for the same unit area during an earlier, similar measurement.

* * * * *